US00PP24396P3

(12) United States Plant Patent
Suphachadiwong

(10) Patent No.: US PP24,396 P3
(45) Date of Patent: Apr. 22, 2014

(54) *PHALAENOPSIS* PLANT NAMED 'SUPHAL1203'

(50) Latin Name: ***Phalaenopsis* hybrid**
Varietal Denomination: SUPHAL1203

(75) Inventor: Thumrong Suphachadiwong, Chonburi (TH)

(73) Assignee: Suphachatwong Innovation Co., Ltd (TH)

( * ) Notice: Subject to any disclaimer, the term of this patent is extended or adjusted under 35 U.S.C. 154(b) by 0 days.

(21) Appl. No.: 13/573,443

(22) Filed: Sep. 14, 2012

(65) Prior Publication Data

US 2014/0082794 P1 Mar. 20, 2014

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell
(74) *Attorney, Agent, or Firm* — Cassandra Bright

(57) ABSTRACT

A new and distinct *Phalaenopsis* cultivar named 'SUPHAL1203' is disclosed, characterized by a compact plant form and significant high flower count per plant. Flowers have light red-purple background coloration and a darker blotch. The new variety is a *Phalaenopsis*, typically produced as an indoor ornamental plant.

1 Drawing Sheet

Latin name of the genus and species: *Phalaenopsis* hybrid. Variety denomination: 'SUPHAL1203'.

BACKGROUND OF THE INVENTION

This application relates to a new cultivar of *Phalaenopsis* hybrid. The new variety is the product of a planned breeding program. The new variety originated as a seedling from the crossing of the unpatented, proprietary seed parent *Phalaenopsis* 'EF' with the unpatented, proprietary pollen parent referred to as *Phalaenopsis* 'WEQS5'. The crossing was made by the inventor in his research greenhouse in Chonburi, Thailand in May of 2002.

The new variety was first selected by the inventor, Thumrong Suphachadiwong, a citizen of Thailand, in December of 2008, in a research in Chonburi, Thailand. After identifying the new variety as a potentially interesting selection, the inventor continued confidential testing and propagation of 'SUPHAL1203' assessing stability of the unique characteristics of this variety.

Asexual reproduction of the new cultivar 'SUPHAL1203' was first performed at a commercial laboratory in Chonburi, Thailand by tissue culture in December of 2008. Access to all plants was restricted, as plants were kept in a greenhouse not open to the public, and tissue culture plantlets were in a laboratory belonging to the inventor, and not accessible to the public. Through subsequent propagation, multiple generations have been reproduced, which have shown that the unique features of this cultivar are stable and reproduced true to type.

SUMMARY OF THE INVENTION

The cultivar 'SUPHAL1203' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUPHAL1203.' These characteristics in combination distinguish 'SUPHAL1203' as a new and distinct *Phalaenopsis* cultivar:

1. Significant high flower count per plant.
2. Unusual compact plant shape.
3. Petals of a light red-purple background color and a darker red-purple blotch.

PARENT COMPARISON

Plants of the new cultivar 'SUPHAL1203' are similar to the seed parent, *Phalaenopsis* 'EF' in most horticultural characteristics. The new variety, however, has faster growth habit than the seed parent.

Plants of the new cultivar 'SUPHAL1203' are similar to the pollen parent, *Phalaenopsis* 'WEQS5' in most horticultural characteristics. Plants of the new variety, however, produce a brighter color than the pollen parent.

COMMERCIAL COMPARISON

'SUPHAL1203' is similar in most horticultural characteristics to the unpatented commercial variety *Phalaenopsis* 'BUENOS AIRES' in most horticultural characteristics. The new variety, however, produces shorter, more erect, lighter green leaves than those of 'BUENOS AIRES'. Additionally, the new variety has a lip and apical lobe of different shape and coloration than that of 'BUENOS AIRES'. Also the new variety produces a slightly smaller flower than 'BUENOS AIRES'.

BRIEF DESCRIPTION OF THE PHOTOGRAPH

The accompanying photograph in FIG. 1 illustrates in full color a typical plant of 'SUPHAL1203' grown in a commercial greenhouse in Zuidbroek, the Netherlands. This plant is approximately 18 months old after deflasking, shown planted in an 11 cm container.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'SUPHAL1203' plants grown in a greenhouse in Zuidbroek, the Netherlands. Temperatures ranged between 18° C. and 28° C. day and night. No photoperiodic or chemical treatments were given to the plants. During bright Summer conditions, shade was given. During dark Winter months, supplemental light was given at unspecified amounts. Measurements and numerical values represent averages of typical plant types.

Botanical classification: *Phalaenopsis* hybrid 'SUPHAL1203'.

PROPAGATION

Type of propagation typically used: Tissue culture.

Time to initiate roots: About 21 days at approximately 28° C.

Time to produce a rooted cutting/liner: About 26 weeks at approximately 18° C. to 28° C.

Root description: Thick (typical for *Phalaenopsis*) and rounded, average diameter: 5 mm, colored greyed-green; near RHS 198D.

PLANT

Growth habit: Monopodial.

Height from to of soil line to top of foliage: Average 11.0 cm.

Height from to of soil line to top of flowers: Average 38.5 cm.

Plant spread: At widest, average: 26.5 cm; at narrowest: 23.0 cm.

Normal pot size: 11 cm.

Growth rate: Moderate.

Number of leaves per plant: Average 6.

FOLIAGE

Leaf:

*Arrangement.*—Distichous.

*Average length.*—Approximately 13.1 cm.

*Average width.*—Approximately 4.9 cm.

*Shape of blade.*—Narrow obovate.

*Aspect.*—Horizontal; young leaves in an average angle of 45° to soil level.

*Apex.*—Unequal acute.

*Base.*—Cuneate. Sheath length: Average 1.3 cm. Sheath width: Average 1.2 cm. Sheath color: Yellow-green; near RHS 148B, strongly tinged greyed-orange; near RHS 177A.

*Margin.*—Entire.

*Texture of top surface.*—Smooth, glossy, slightly furrowed.

*Texture of bottom surface.*—Smooth, glossy, very slightly furrowed.

*Color.*—Young foliage upper side: Yellow-green; near RHS 144A, outer margin greyed-purple; near RHS N186C. Young foliage under side: Yellow-green; near RHS 146C, strongly tinged greyed-purple towards the margins; near RHS N186C. Mature foliage upper side: Yellow-green; near RHS 144A outer margin greyed-purple; near RHS N186C. Mature foliage under side: Yellow-green; near RHS 146C, outer margins moderately to strongly tinged greyed-purple; near RHS N186C.

*Venation.*—Type: Camptodromous. Venation coloration: Yellow-green; in between near RHS 144A and 146B, main vein on under side greyed-purple; near RHS N186C, especially in young leaves.

Petiole: No petioles present.

FLOWERING CHARACTERISTICS

Flower bud:

*Rate of opening.*—Approximately 5 days after stage described.

*Length.*—Approximately 1.4 cm.

*Diameter.*—Approximately 1.1 cm wide and 1.3 cm high.

*Shape.*—Broad ovate.

*Color.*—Purple to greyed-purple; in between near RHS N77D and 186C, striped red-purple; near RHS 70B, under side greyed-white; near RHS 156C.

Peduncle:

*Length.*—Approximately 34.5 cm.

*Width.*—Approximately 0.4 cm.

*Aspect.*—Approximately 65° angle to rosette.

*Strength.*—Strong.

*Texture.*—Smooth, not very glossy.

*Color.*—Yellow-green; near RHS 146A, heavily marbled greyed-purple to brown; in between near RHS 186C and 200C.

Inflorescence:

*Flowers per stem.*—Average 40.

*Inflorescence arrangement.*—Panicle.

*Inflorescence height.*—Approximately 22.3 cm (measured from lowest branching of panicle to top of inflorescence).

*Inflorescence width.*—Approximately 22.2 cm.

Individual flowers:

*Flower type.*—Single zygomorphic. Shape: Wide elliptic. Length (height): Approximately 4.7 cm. Width: Approximately 4.6 cm. Depth: Approximately 3.0 cm. Fragrance: No fragrance. Persistent: Non-persistent. Quantity of petals: 2.

*Petals.*—Arrangement: One petal on each side of the column. Length: Approximately 2.5 cm. Width: Approximately 2.4 cm. Shape: Deltoid. Apex: Rounded. Base: Cuneate. Margin: Entire. Texture: Upper (forward) surface: smooth, dull, moderately velvety. Texture: Lower (back) surface: smooth, dull, moderately velvety. Color: When opening, forward surface: Purple; near RHS N78B, margin white, near RHS N155C. When opening, back surface: Purple; near RHS N78D, margin white, near RHS N155C. Fully Opened, forward surface: Purple; in between near RHS N78B and N78C, margin white, near RHS N155D. Fully Opened, back surface: Purple to purple-violet; near RHS N78D and N80D, margin white, near RHS N155D. Fading, forward surface:

purple-violet; near RHS N80D, margin white, near RHS N155B. Fading, back surface: purple-violet; near RHS N80D, margin white, near RHS N155B. Color Venation Fully Opened, forward surface: No venation visible. Fully Opened, back surface: Main vein colored red-purple; near RHS 72B.

*Labellum.*—Shape: Three-parted. Length: Approximately 2.0 cm. Width: Approximately 1.6 cm. Texture: Smooth, dull, slightly velvety. Tip: Cleft. Base: Cuneate. Color: When opening, forward surface: Central lobe red-purple; near RHS 60C, colored purple towards the top; near RHS N78A, outer tip white; near RHS N155D, margins near the base colored orange; near RHS 26A. Lateral lobes red-purple; near RHS N78A, lighter towards the top; near RHS N78B, base white; near RHS 155A, dotted red-purple; near RHS 59A. Callosities yellow; near RHS 3C, dotted red-purple; near RHS 59A. When opening, back surface: Central lobe purple; near RHS 76C To 76D, margins of lower half colored yellow-orange; near RHS 16B, flushed red-purple; margins of upper half red-purple; near RHS 72B, top white; near RHS NN155D. Lateral lobes red-purple; near RHS N78A to N78B, base white; near RHS 155D. Fully Opened, forward surface: Central lobe red-purple; near RHS 60C, colored purple towards the top; near RHS N78A, outer tip white; near RHS N155D. Lateral lobes red-purple; near RHS N78B, base white; near RHS N155A, dotted red-purple; near RHS 59A. Callosities yellow; near RHS 5A, dotted red-purple; near RHS 59A. Fully Opened, back surface: Central lobe purple; near RHS 76C To 76D, margins of lower half colored yellow-orange; near RHS 16B, flushed red-purple; margins of upper half red-purple; near RHS 72B, top white; near RHS N155D. Lateral lobes red-purple; near RHS N78B, base white; near RHS N155A. Fading, forward surface: Purple-violet; near RHS N80B. Fading, back surface: Purple-violet; near RHS N80C to N80D. Color Venation Fully Opened, forward surface: No venation visible. Fully Opened, back surface: No venation visible. Margin: Entire.

Sepals:

*Quantity.*—3.

*Appearance.*—Smooth, dull, moderately velvety.

*Length.*—Approximately 2.5 cm.

*Width.*—Approximately 1.7 cm.

*Shape.*—Ovate to elliptic.

*Apex.*—Obtuse.

*Base.*—Broad cuneate.

*Margin.*—Entire.

*Texture.*—Smooth, dull, moderately velvety.

*Color.*—Fully Opened, forward surface: Lower half purple; in between near RHS N78C to N78D, veined darker; near RHS N78B, upper half white; near RHS N155D. Lower half of lateral sepals dotted red-purple; near RHS 71A. Fully Opened, back surface: Purple; near RHS 77C and 77D, with a red-purple main vein; near RHS 72B, margin white, near RHS N155C.

Pedicels:

*Length.*—Approximately 2.9 cm.

*Diameter.*—Approximately 0.3 cm.

*Angle.*—Approximately 85° to peduncle.

*Strength.*—Moderately strong.

*Texture.*—Smooth, moderately glossy.

*Color.*—Yellow-green; near 146C, distal part purple; 75B, 75C and 75D.

REPRODUCTIVE ORGANS

*Stamens, style and stigma fused into column.*—Yes.

*Column length.*—Approximately 1.0 cm.

*Column diameter.*—Approximately 0.5 cm.

*Column color.*—Upper side purple; near RHS N78B, under side lighter; near RHS N78D.

*Ovary.*—Position: Inferior. Diameter: Approximately 0.3 cm. Color: Green-white; near RHS 157D.

*Pollinia color.*—Yellow-orange; near RHS 21A.

OTHER CHARACTERISTICS

Disease resistance: Neither resistance nor susceptibility to the normal diseases found in *Phalaenopsis* has been observed.

Drought tolerance and cold tolerance: Normal for species.

Fruit/seed production: No fruits/seeds detected to date.

What is claimed is:

1. A new and distinct cultivar of *Phalaenopsis* plant named 'SUPHAL1203' as herein illustrated and described.

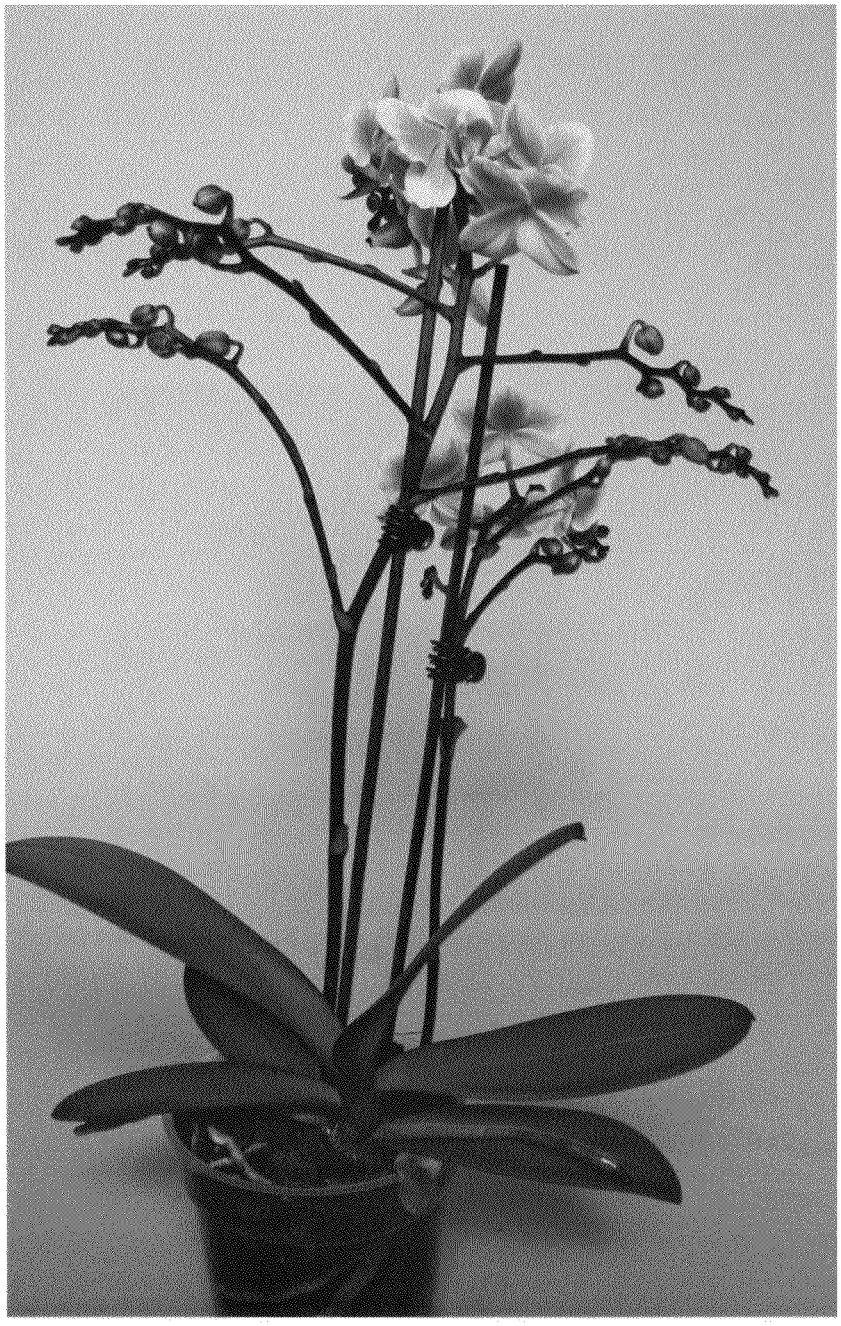

* * * * *